United States Patent
Liu et al.

(10) Patent No.: US 10,026,168 B2
(45) Date of Patent: Jul. 17, 2018

(54) MEDICAL SCANNING SYSTEM AND METHOD FOR DETERMINING SCANNING PARAMETERS BASED ON A SCOUT IMAGE

(71) Applicant: General Electric Company, Schenectady, NY (US)

(72) Inventors: Ping Liu, Beijing (CN); Jiaqin Dong, Beijing (CN); Jie Wu, ChangDu (CN)

(73) Assignee: General Electric Company, Schenectady, NY (US)

( * ) Notice: Subject to any disclaimer, the term of this patent is extended or adjusted under 35 U.S.C. 154(b) by 37 days.

(21) Appl. No.: 15/124,336

(22) PCT Filed: Mar. 10, 2015

(86) PCT No.: PCT/US2015/019669
§ 371 (c)(1),
(2) Date: Sep. 7, 2016

(87) PCT Pub. No.: WO2015/138428
PCT Pub. Date: Sep. 17, 2015

(65) Prior Publication Data
US 2017/0018078 A1    Jan. 19, 2017

(30) Foreign Application Priority Data
Mar. 11, 2014    (CN) .......................... 2014 1 0087904

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/488* (2013.01); *A61B 6/545* (2013.01); *G06K 9/6207* (2013.01);
(Continued)

(58) Field of Classification Search
None
See application file for complete search history.

(56) References Cited

U.S. PATENT DOCUMENTS

2008/0159611 A1    7/2008  Tao et al.
2010/0278405 A1*  11/2010  Kakadiaris .......... G06F 19/3431
                                                    382/131
2014/0147026 A1*   5/2014  Liu ....................... G06T 7/0032
                                                    382/131

FOREIGN PATENT DOCUMENTS

JP    2012045192 A    3/2012
WO   2002028284 A1   4/2002
WO   2008141996 A2  11/2008

OTHER PUBLICATIONS

International Search Report and Written Opinion for corresponding PCT application PCT/US2015/019669 dated May 28, 2015; 10 pages.

* cited by examiner

*Primary Examiner* — Idowu O Osifade
(74) *Attorney, Agent, or Firm* — McCoy Russell LLP (57) ABSTRACT

A medical scanning system and method for determining scanning parameters based on a scout image, the system includes: a scanned object description module for describing the shape of a scanned object on an initial image; an adjustment module for aligning the shape of the scanned object with the pre-stored average shape; a principal component analysis module for extracting the principal component for the aligned shape of the scanned object; a desired shape acquisition module for imparting weight parameters to said principal component, acquiring a plurality of new shapes, and from said plurality of new shapes, determining the new shape with the maximum cost function value as the (Continued)

desired shape and a scanning parameter setting module for setting scanning parameters based on the desired shape.

14 Claims, 6 Drawing Sheets

(51) Int. Cl.
*G06K 9/62* (2006.01)
*A61B 6/00* (2006.01)
*G06T 7/33* (2017.01)
*G06T 7/11* (2017.01)
*G06K 9/36* (2006.01)

(52) U.S. Cl.
CPC .............. *G06K 9/6209* (2013.01); *G06T 7/11* (2017.01); *G06T 7/33* (2017.01); *A61B 6/505* (2013.01); *G06K 2009/366* (2013.01); *G06T 2207/10116* (2013.01); *G06T 2207/30012* (2013.01)

MEDICAL SCANNING SYSTEM AND METHOD FOR DETERMINING SCANNING PARAMETERS BASED ON A SCOUT IMAGE

This application is a filing under 35 U.S.C. 371 of international application number PCT/US2015/019669, filed Mar. 10, 2015, which claims priority to China application number 201410087904.2, filed Mar. 11, 2014, the entire disclosure of each of which is hereby incorporated by reference.

TECHNICAL FIELD

The present invention relates generally to the field of medical diagnosis, and more particularly, to a medical scanning system and method for determining scanning parameters based on a scout image.

BACKGROUND ART

Figure 1:
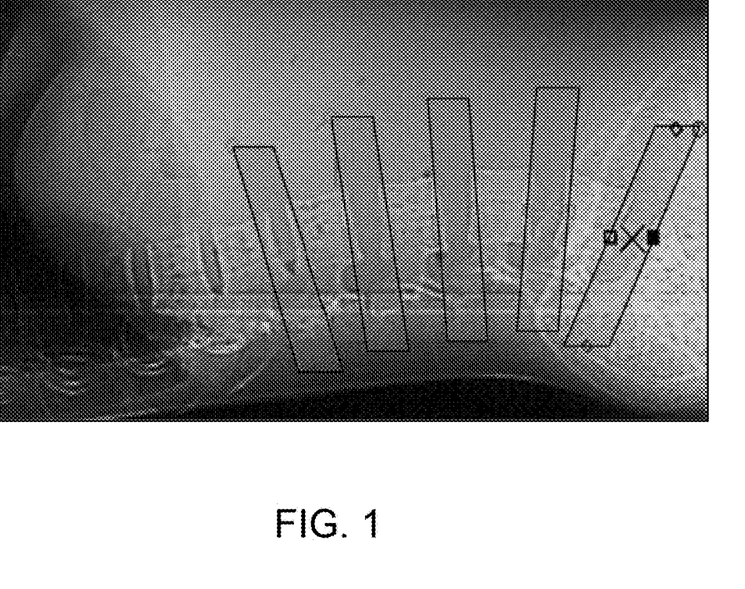
FIG. 1 is a schematic diagram of manual adjustment of scanning parameters based on a scout image in the prior art.

At present, the diagnosis of diseases for various body parts is done by Computer Tomography (CT) technologies. Taking lumbar disc as an example, diagnostic images of individual lumbar discs may typically be acquired by first scanning the entire lumbar to acquire a scout image as shown in FIG. 1 before a single lumbar disc is scanned axially, determining and adjusting scanning parameters, such as scanning position, scanning angle, scanning range and display field of view, etc., during the lateral scan, based on the scout image, and scanning axially based on the adjusted scanning parameters. For example, adjusting respectively the position, width and angle, etc. of each of five rectangle portions shown in FIG. 1 may respectively determine different scanning positions, scanning angles and scanning ranges for these five lumbar discs.

However, in the state of the art, scanning parameters are required to be adjusted manually, which has the following problems:

Firstly, upon manual adjustment of the above-mentioned scanning parameters, the accuracy that will be achieved by different operators may be different, inexperienced operation will cause relatively low accuracy of scanning parameters, thereby influence the precision of diagnostic results.

Secondly, although some experienced operators may accurately adjust scanning parameters, the time required for the adjustment is longer, as known from clinical experiments, for each lumbar disc, an operator will operate (e.g., click, drag, and the like) the mouse at least 5-6 times, and thus, for 5 lumbar discs, up to 25-30 times, in order to complete the parameter adjustment, leading to a troublesome operation and longer time for the operation, for a less experienced operator, the time required for the operation is much longer, thus reducing the efficiency of operation.

Therefore, there is a need for a new medical scanning system and method that can automatically determine scanning parameters based on a scout image, thereby reducing the time required for adjusting scanning parameters, and improving the precision.

SUMMARY OF THE INVENTION

Exemplary embodiments of the present invention provides a medical scanning system for determining scanning parameters based on a scout image, comprising a scanned object description module, an adjustment module, a principal component analysis module, a desired shape acquisition module and a scanning parameter setting module. The scanned object description module is to arrange a plurality of control points for describing the shape of a scanned object on an initial scout image; the adjustment module is to align the shape of the scanned object with previously stored average shape by linearly transforming control points for the shape of the scanned object; the principal component analysis module is to extract the principal component of the aligned shape of the scanned object by means of a principal component analysis algorithm; the desired shape acquisition module is to impart a plurality of weight parameters to the principal component, acquire a plurality of new shapes by means of the following equation, and determine, from the acquired plurality of new shapes, the new shape with the maximum cost function value as the desired shape:

$$s' = \bar{s} + P_s b_{new},$$

where, s' is used to describe the above new shape, $\bar{s}$ is used to describe the average shape, Ps represents the principal component, bnew represents the weight parameter of the principal component; the scanning parameter setting module is to set the scanning parameter based on the desired shape.

Exemplary embodiments of the present invention is also to provide a medical scanning method of determining scanning parameters based on the scout image. The method includes the steps of: arranging a plurality of control points for describing the shape of a scanned object on an initial scout image; aligning the shape of the scanned object with the previously stored average shape by linearly transforming control points for describing the shape of a scanned object; extracting the principal component of the aligned shape of the scanned object by means of a principal component analysis algorithm; imparting a plurality of weight parameters to the principal component, acquiring a plurality of new shapes by means of the following equation, and determining, from the acquired plurality of new shapes, the new shape with the maximum cost function value as the desired shape:

$$s' = \bar{s} + P_s b_{new},$$

where, s' is used to describe the above new shape, $\bar{s}$ is used to describe the average shape, Ps represents the principal component, bnew represents the weight parameter of the principal component; setting scanning parameters based on the desired shape.

Other features and aspects will become apparent upon reading of the following detailed description, accompanying drawings and claims.

BRIEF DESCRIPTION OF DRAWINGS

The present invention will be better appreciated from exemplary embodiments thereof, as described below, taken in conjunction with the accompanying drawings, in which.

DESCRIPTION OF EMBODIMENTS

Specific embodiments of the present invention will be described below. It should be pointed out that, during the specific description of these embodiments, for purpose of brief description, it is impossible that the specification will exhaustively describe all features of actual embodiments. It should be appreciated that, during practice of any one of embodiments, as in the process of any one of engineering projects or design projects, to implement a specific purpose of a developer and to meet system-related or commerce-related limitations, various specific decisions may often be made and vary from one embodiment to another embodiment. Furthermore, it may also be appreciated that, although efforts made during this kind of development might be complicated and tedious, for those skilled in the field of what is disclosed according to the present invention, some alternations in terms of design, manufacture or production and the like on the basis of technical contents revealed according to this disclosure are only regular technical means, and should not be considered as insufficient content of this disclosure.

Unless defined otherwise, technical or scientific terms as used in claims and the specification should have the same meaning as commonly understood by one of ordinary skilled in the art to which the present invention belongs. Such words as first, second, third as used in the specification and claims of the present invention patent application does not represent any order, quantity or importance, which can be simply used to distinguish between different component parts. The indefinite article "a" or "an" and the like does not denote a limitation of quantity, but rather denote the presence of at least one. Such words as "include" or "comprise" is meant to indicate that elements or things preceding "include" or "comprise" would cover those listed after such words or equivalent elements thereof, and do not exclude other elements or things Such words as "connect" or "connected" are not limited to physical or mechanical connection, nor to direct or indirect connection.

Figure 2:
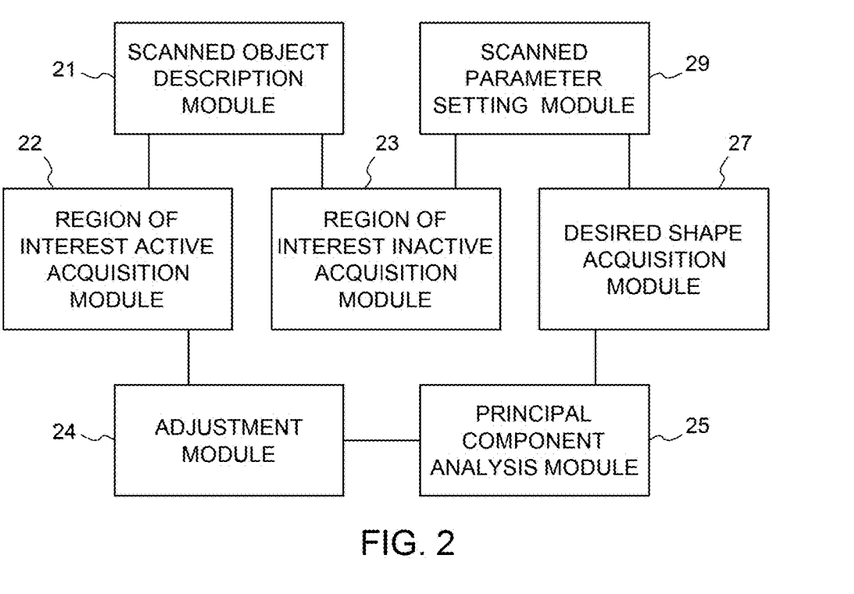
FIG. 2 is a structural block diagram of a medical scanning system for determining scanning parameters based on a scout image provided in accordance with one embodiment of the present invention.
Figure 3:
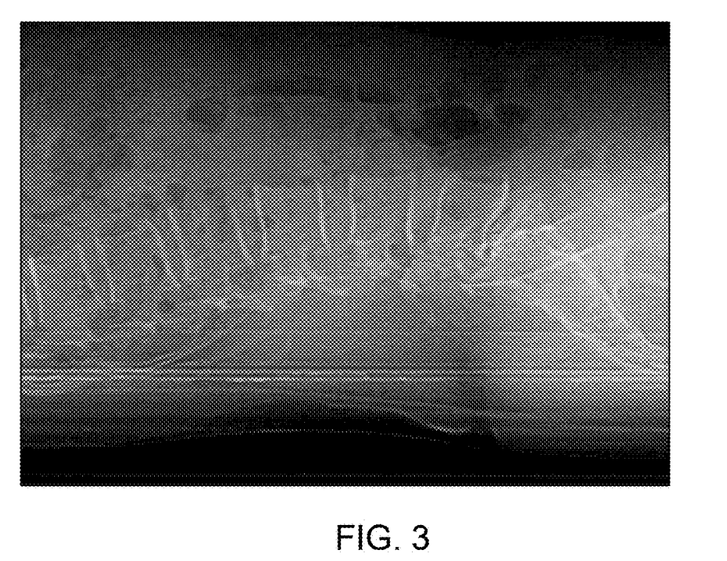
FIG. 3 is an initial scout image provided in accordance with one embodiment of the present invention.
Figure 4:
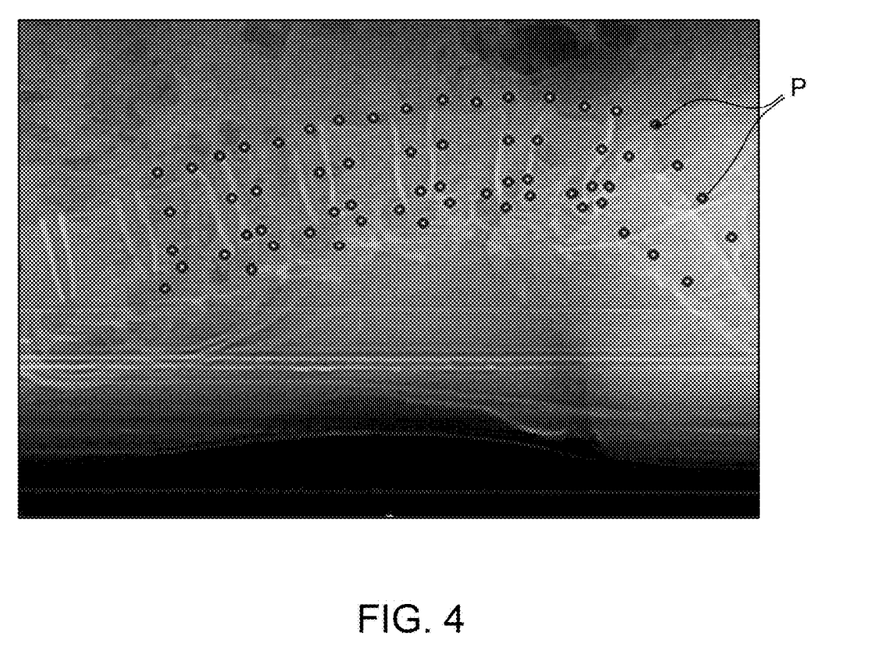
FIG. 4 is a schematic diagram of utilization of a plurality of control points for describing the shape of the scanned object in the initial scout image shown in FIG. 3.
Figure 5:
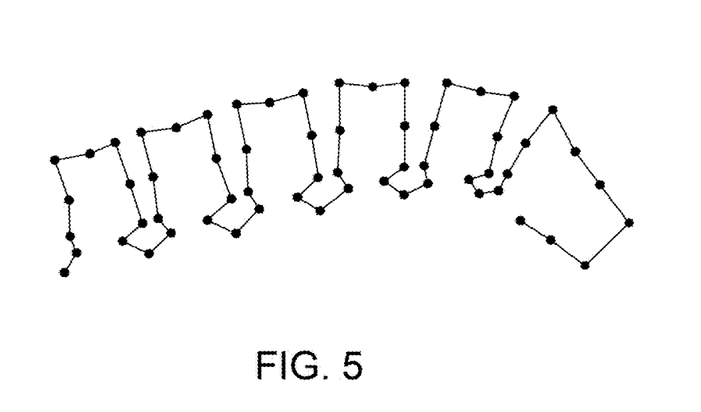
FIG. 5 is a schematic diagram of the shape of the scanned object that is formed of a plurality of control points in FIG. 4.

FIG. 2 is a structural block diagram of a medical scanning system for determining scanning parameters based on a scout image provided in accordance with one embodiment of the present invention, and FIG. 3 is an initial scout image provided in accordance with one embodiment of the present invention, in the initial scout image, there is a scanned object, such as lumbar. FIG. 4 is a schematic diagram of utilization of a plurality of control points for describing the shape of a scanned object in the scout image as shown in FIG. 3; and FIG. 5 is a schematic diagram of the shape of the scanned object that is formed of a plurality of control points in FIG. 4.

As shown in FIG. 2, the medical scanning system includes a scanned object description module 21, an adjustment module 24, a principal component analysis module 25, a desired shape acquisition module 27 and a scanning parameter setting module 29.

As shown in FIG. 4, the scanned object description module 21 is used for arranging a plurality of control points P on an initial scout image, these control points P being used for describing the shape of the scanned object. In the embodiment, the scanned object is a lumbar, the scanned object description module 11 is particularly to describe the shape of the lumbar through 61 control points P, to form the shape as shown in FIG. 5.

In the embodiment, the average shape of the scanned object may be stored in advance, the average shape may be obtained by analyzing a great number of samples of the scout image, and particularly, control points are arranged in each of samples to describe the shape of the scanned object therein, and the average shape is acquired by performing mean value calculation of shapes in all samples. Control points in each of samples correspond with control point on the initial scout image in quantities and there is a one-to-one correspondence between them.

The above average shape may particularly be described by equation (1) below:

$$\bar{S} = \frac{1}{N}\sum_{i=1}^{N} s_i \quad (1)$$

In equation (1) above, N represents the number of samples of a scout image, si is used for describing the shape of the scanned object in the ith sample, $1 \le i \le N$.

The adjustment module 24 is to align the shape of the scanned object with the previously stored average shape by linearly transforming control points for the shape of the above-mentioned scanned object. Particularly, control points P have fixed coordinate values in the initial scout image, the previously stored average shape is also described by means of control points P corresponding to control points P one by one, control points of the average shape also have fixed coordinate values, the adjustment module 14 is to align control points P with control points of the average shape by linearly transforming control points P for describing the shape of the scanned object, thereby implementing alignment of the shape of the scanned object with the average shape.

In the embodiment, the adjustment module 24, particularly, linearly transforms the control points for the shape of the scanned object by means of equation (2) below.

$$\begin{pmatrix} x' \\ y' \end{pmatrix} = \begin{bmatrix} s_x & 0 \\ 0 & s_y \end{bmatrix} \begin{bmatrix} \cos\theta & -\sin\theta \\ \sin\theta & \cos\theta \end{bmatrix} \begin{pmatrix} x \\ y \end{pmatrix} + \begin{pmatrix} t_x \\ t_y \end{pmatrix} \quad (2)$$

In equation (2) above, x' and y' respectively represent abscissa values and ordinate values of the linearly transformed control points P for describing the shape of the scanned object on the initial scout image, x and y respectively represent abscissa values and ordinate values of control points P for describing the shape of the scanned object, before being linearly transformed, on the initial scout image, sx and sy respectively represent the scaling coefficient for the shape of the scanned object, θ represents the rotation angle for the shape of the scanned object, tx and ty respectively represent translation sizes of control points P for describing the shape of the scanned object in abscissa direction and ordinate direction.

Based on the above description, the adjustment module 24 may linearly transform control points P for describing the shape of the scanned object directly based on the initial scout image. A region of interest may further be determined in the initial scout image as the image of interest, so that the adjustment module 24 linearly transforms control points P based on the image of interest. The region of interest may be a region in which the scanned object is distributed.

Figure 6:
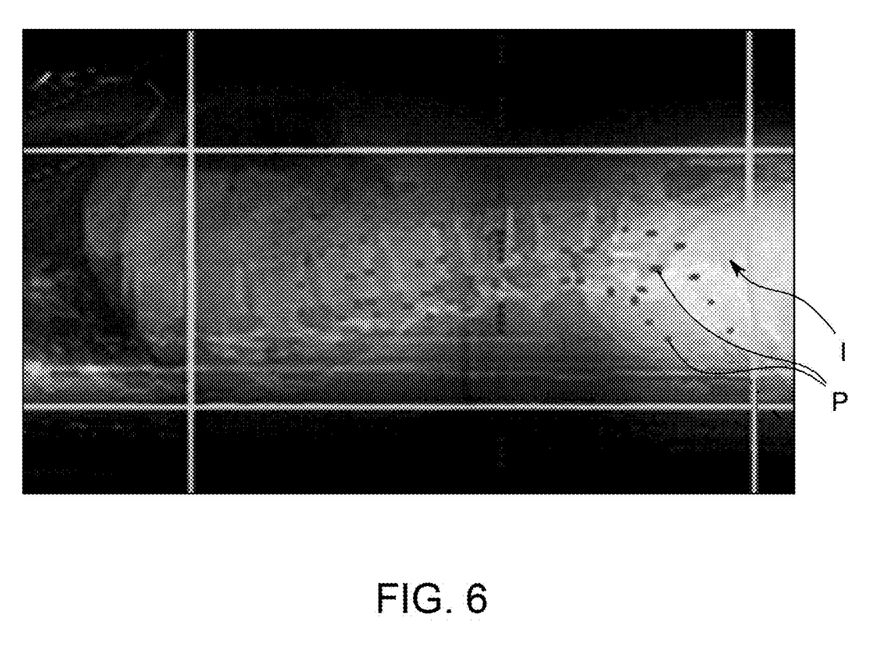
FIG. 6 is a schematic diagram of acquisition of the region of interest in the initial scout image by utilizing a gray-scale projection method in accordance with one embodiment of the present invention.

FIG. 6 is a schematic diagram of acquisition of the region of interest in the initial scout image by utilizing a gray-scale projection method in accordance with one embodiment of the present invention. For example, in the medical scanning system of the embodiment, there is further provided a region of interest active acquisition module 22, which automatically determines, in the initial scout image, the region of interest I as the image of interest by means of a gray-scale projection method, so that the adjustment module 24 linearly transforms the control points based on the image of interest. Utilizing the gray-scale projection method may locate the scanned object, further using the region in the initial scout image, in which the scanned object is distributed as the region of interest, the gray-scale projection method is a known image processing method and the description thereof will be not repeated here.

Figure 7:
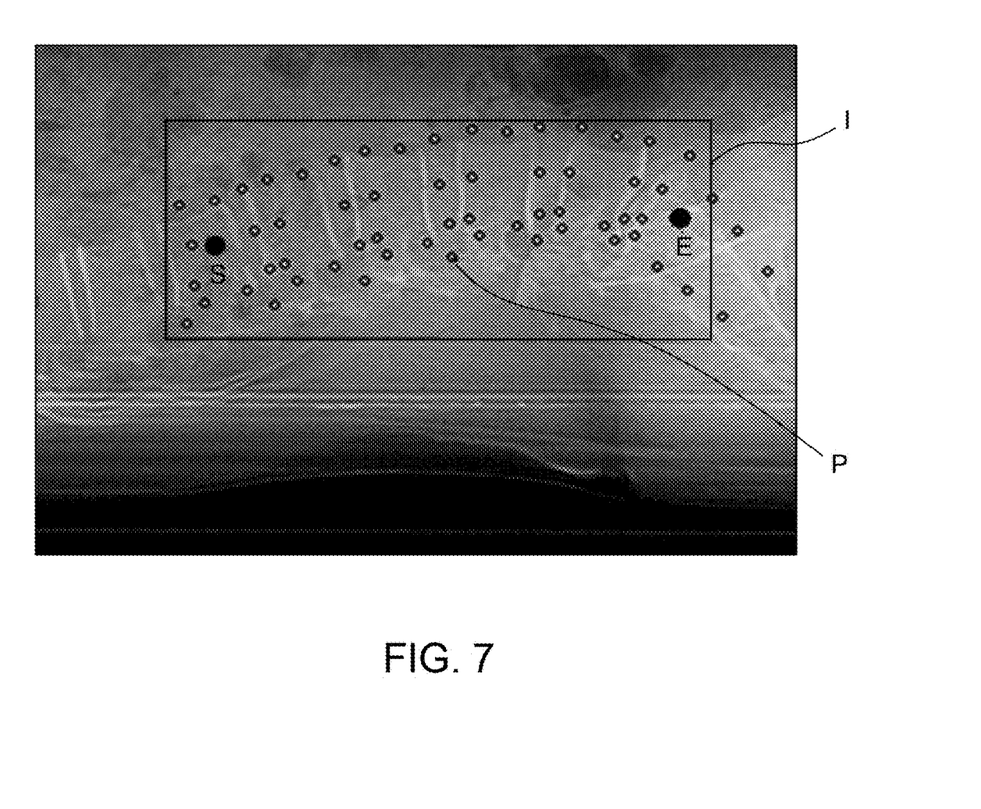
FIG. 7 is a schematic diagram of acquisition of the region of interest in the initial scout image by setting the starting point and the end point in accordance with one embodiment of the present invention.

FIG. 7 is a schematic diagram of acquisition of the region of interest in the initial scout image by setting the starting point and the end point in accordance with one embodiment of the present invention. For example, in the medical scanning system of the embodiment, there is further provided a region of interest inactive acquisition module 23, which sets the starting point S and the end point E in the initial scout image based on operation instructions from the operating device, and defines a region I as the image of interest in the initial scout image based on said starting point S and said end point E, so that the adjustment module 24 may linearly transform control points P based on the image of interest, e.g., determining boundaries of the region of interest near the starting point S and the end point E. The above-mentioned operating device may particularly be an input device such as a mouse, a keyboard and the like that is required to be operated by an operator manually.

With the region of interest active acquisition module 22, the region of interest can be automatically determined without manual operation by an operator. And with the region of interest inactive acquisition module 23, the complexity of operation may be reduced by setting the starting point and the end point based on operation instructions. In actual application, the region of interest active acquisition module 22 or the region of interest inactive acquisition module 23 may be selectively executed as needed, to obtain the image of interest.

The principal component analysis module 25 is to exact the principal component of the aligned shape of the scanned object by means of a Principal Component Analysis (PCA) algorithm. The principal component analysis algorithm is also referred to as the principal components analysis, which is a multivariate statistical analysis method for selecting less number of significant variables by linearly transforming a number of variables that is a known algorithm and the description thereof will not be repeated here. In the embodiment, the principal component obtained by the principal component analysis module 25 through the principal component analysis algorithm is: $P_s=(p_1\ p_2\ \ldots\ p_m)$, which has m variables, these m variables are regarded as the variables that may have the largest impact on the aligned shape of the scanned object, m being an integer larger than 0.

By analyzing the principal components for the shape of the scanned object, this makes it possible to avoid the problem of excessive heavy computation due to excessive number of shape component variables, and shorten the duration for determining scanning parameters.

The desired shape acquisition module 27 is to impart a plurality of weight parameters bnew to the above-mentioned principal components, and acquire a plurality of new shapes by equation (3) below:

$$s'=\bar{s}+P_s b_{new} \tag{3}$$

In equation (3) above, s' is used to describe the new shape, $\bar{s}$ is used to describe the average shape, Ps represents the principal component, and bnew represents the weight parameter of the principal component.

The desired acquisition module 27 will further determine, from the acquired plurality of new shapes, the new shape with the maximum cost function value as the desired shape.

As an alternative, the desired shape acquisition module 27 may determine the new shape with the maximum cost function value by means of an optimization algorithm, which is also a known algorithm and the description thereof will not be repeated here.

To reduce the complexity of operation, as an alternative, the desired shape acquisition module 27 may further include a coarse selection module and at least one fine selection module to determine the new shape with the maximum cost function value by means of multi-order selection method. In which the coarse selection module first imparts a plurality of weight parameters to the principal component Ps within the preset varying range of numerical values (e.g., −10 to 10), and determines, from the currently acquired plurality of new shapes, the new shape with the maximum cost function value as the better shape.

Each fine selection module is, centered on the weight parameter (e.g., 5) corresponding to the previous better shape, to impart a plurality of weight parameters bnew to the principal component Ps within a varying range of numerical values that is less than the previous varying range of numerical values, and from the currently acquired plurality of new shapes, determine the new shape with the maximum cost function value as the better shape, wherein the last acquired better shape is determined to be the desired shape.

For example, when the number of the fine selection modules is 2, the first fine selection module is, centered on the weight parameter 5, to impart a plurality of weight parameters bnew to the principal component Ps within the varying range of numerical values between 2 and 8, and from the currently acquired plurality of new shapes, determine the new shape desired for the cost function value as the second better shape, which is used as the center of the varying range of numerical values determined by the second fine selection module.

The second fine selection module is, centered on the weight parameter (e.g., 6) corresponding to the second better shape, to impart a plurality of weight parameters bnew to the principal component Ps within a smaller varying range of numerical values (e.g., 5 to 7), and from the currently acquired plurality of new shapes, determine the new shape desired for the cost function value as the third better shape, i.e., desired shape.

The scanning parameter setting module 29 is used to set scanning parameters based on the desired shape acquired by the desired shape acquisition module 27, for example, adjusting parameters such as scanning position, scanning range, scanning angle and display field of view upon each of axial scans. After scanning parameters are set, axial scan may be done to obtain a better axial scanning image.

Figure 8:
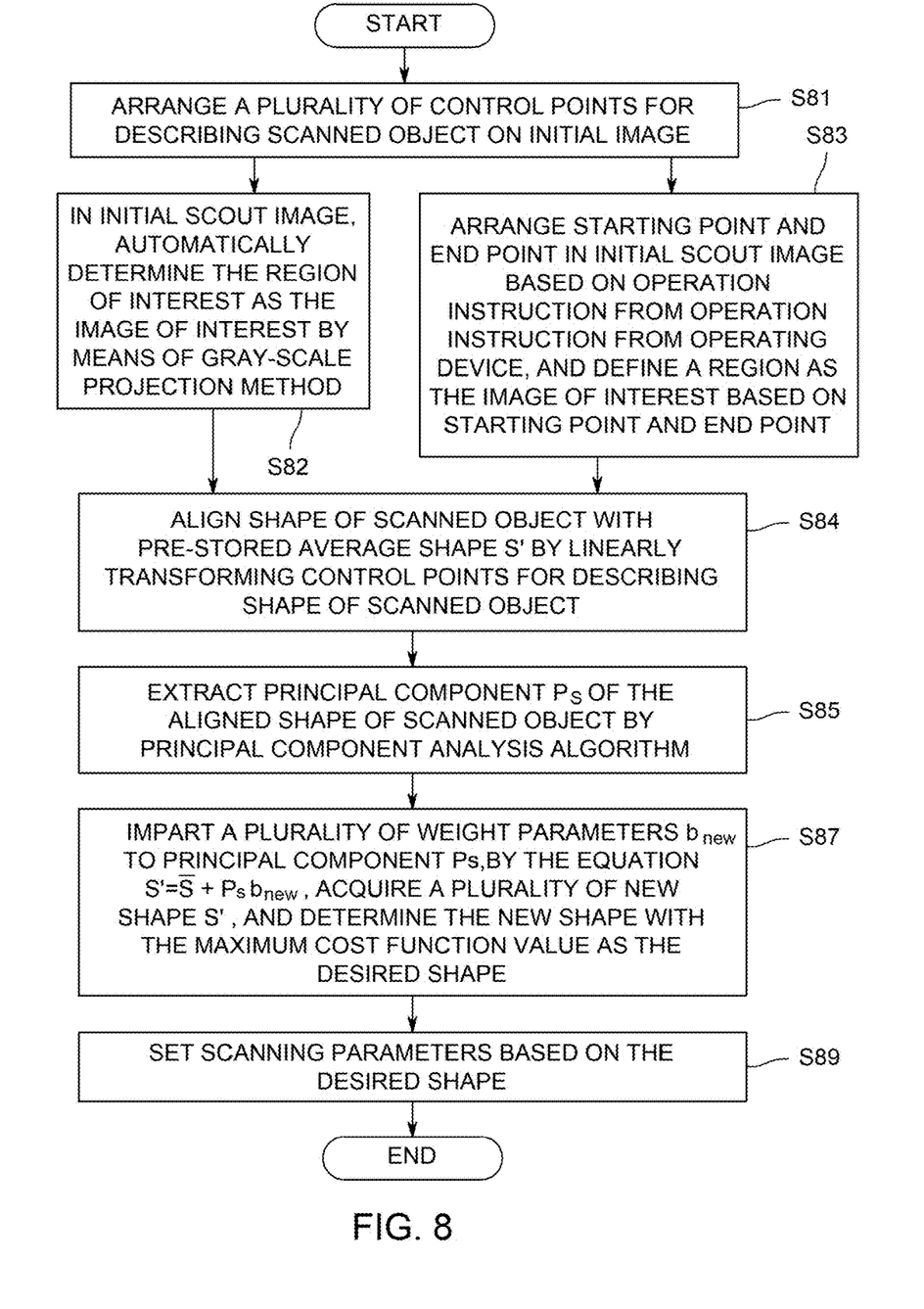
FIG. 8 is a flow chart of a medical scanning method of determining scanning parameters based on a scout image provided in accordance with one embodiment of the present invention.

FIG. 8 is a flow chart of a medical scanning method of determining scanning parameters based on a scout image provided in accordance with one embodiment of the present invention. The method may be applied to the medical scanning system shown in FIG. 2. As shown in FIG. 8, the method includes a scanned object description step S81, an adjustment step S84, a principal component analysis step S85, a desired shape acquisition step S87 and a scanning parameter setting step S89.

Scanned object description step S81: arrange a plurality of control points for describing the scanned object on the initial scout image. For example, arrange a plurality of control points P on the initial scout image shown in FIG. 3, to describe the shape of the lumbar therein, forming the shape as shown in FIG. 4.

Adjustment step S84: align the shape of the scanned object with the previously stored average shape $\bar{s}$ by linearly transforming control points for describing the shape of the above-mentioned scanned object. The above-mentioned shape $\bar{s}$ may be obtained by analyzing a great number of samples of the scout image, control points are arranged in various samples to describe the shape of the scanned object therein, and the average shape is acquired by performing mean calculation of shapes in all samples, the average shape may be particularly described by equation (1), this step particularly linearly transforms the control points for the shape of the scanned object by equation (2) above.

Principal component analysis step S85: extract the principal component $P_s$ of the aligned shape of the scanned object by means of a principal component analysis algorithm.

Desired shape acquisition step S87 impart a plurality of weight parameters bnew to the principal component Ps, acquire a plurality of new shapes s' by equation (3), and determine, from the acquired plurality of new shapes, the new shape with the maximum cost function value as the desired shape.

Scanning parameter setting step S89: set scanning parameters based on the desired shape.

Optionally, the region of interest active acquisition step S82 or the region of interest inactive acquisition step S83 is also provided between the scanned object description step S81 and the adjustment step S84.

Region of interest active acquisition step S82: automatically determine, in the initial scout image, the region of interest as the image of interest by means of gray-scale projection method.

Region of interest inactive acquisition step S83: set the starting point and the end point in the initial scout image based on operation instruction of the operating device, and define one region as the image of interest based on the starting point and the end point.

By means of the active acquisition step S82 or the region of interest inactive acquisition step S83, it is possible for the adjustment step S84 to linearly transform control points P for describing the shape of the scanned object based on the image of interest.

The desired shape acquisition step S87 may determine the new shape with the maximum cost function value as the desired shape by means of an optimization algorithm. The desired shape acquisition step S87 may also include a coarse selection step and at least one fine selection step to determine the new shape with the maximum cost function value:

Coarse selection step: first impart a plurality of weight parameters to the principal component within the preset varying range of numerical values, and determines, from the currently acquired plurality of new shapes, the new shape with the maximum cost function value as the better shape.

At least one fine selection step: each fine selection step is, centered on the weight parameter corresponding to the previous better shape, to impart a plurality of weight parameters to said principal component within a varying range of numerical values that is less than the previous varying range of numerical values, and from the currently acquired plurality of new shapes, determine the new shape with the maximum cost function value as the better shape, wherein the last acquired better shape is determined to be the desired shape.

The medical scanning system and method provided in accordance with embodiments of the present invention for determining scanning parameters based on the scout image is to describe the shape of the scanned object by arranging control points on the scout image, align the shape with the pre-stored shape in order to analyze the principal component for the shape of the scanned object, obtain the shape desired for the scanned object by imparting the weight value to the principal component and incorporating the average shape, so as to be able to determine the distribution range, angle and the like of various parts in the scanned object based on the desired shape, thereby rapidly and accurately setting corresponding scanning parameter, and avoiding problems of low accuracy, longer operating duration and the like caused by manual operation.

Some exemplary embodiments have been described above. However, it should be appreciated that various modifications may be made. For example, if the described technologies are performed in different order and/or if the described system, architecture, equipment or circuit are differently combined and/or are replaced or supplemented with other component or equivalent thereof, appropriate result may be achieved. Accordingly, other embodiments may also be fallen within the claimed scope.

What is claimed is:

1. A medical scanning method for determining scanning parameters, comprising:
acquiring an initial scout image;
arranging a plurality of control points for describing a shape of a scanned object on the initial scout image;
aligning the shape of the scanned object with a previously stored average shape by linearly transforming the plurality of control points for describing the shape of the scanned object;
extracting a principal component of the aligned shape of the scanned object based on a principal component analysis algorithm;
acquiring a plurality of new shapes based on the principal component of the aligned shape of the scanned object via the following equation:

$$s'=\bar{s}+P_s b_{new}$$

where, s' is used to describe a new shape, $\bar{s}$ is used to describe an average shape, Ps represents the principal component, $b_{new}$ represents a weight parameter of the principal component;
determining a desired shape with a maximum cost function value based on the plurality of new shapes; and
setting scanning parameters based on the desired shape.

2. The medical scanning method for determining scanning parameters according to claim 1, further comprising automatically determining a region as an image of interest based on a gray-scale projection method, and linearly transforming the plurality of control points for describing the shape of the scanned object based on the image of interest.

3. The medical scanning method for determining scanning parameters according to claim 1, further comprising setting a starting point and an end point in the initial scout image based on operation instruction of an operating device, defining, in the initial scout image, a region as an image of interest based on the starting point and the end point, and transforming the plurality of control points for describing the shape of the scanned object based on the image of interest.

4. The medical scanning method for determining scanning parameters according to claim 1, wherein a control point of the plurality of control points for describing the shape of the scanned object is linearly transformed based on the following equation:

$$\begin{pmatrix} x' \\ y' \end{pmatrix} = \begin{bmatrix} s_x & 0 \\ 0 & s_y \end{bmatrix} \begin{bmatrix} \cos\theta & -\sin\theta \\ \sin\theta & \cos\theta \end{bmatrix} \begin{pmatrix} x \\ y \end{pmatrix} + \begin{pmatrix} t_x \\ t_y \end{pmatrix}$$

where, x' and y' respectively represent abscissa values and ordinate values of the linearly transformed control point for describing the shape of the scanned object on the initial scout image, x and y respectively represent abscissa values and ordinate values of the control point for describing the shape of the scanned object, before being linearly transformed, on the initial scout image, $s_x$ and $s_y$ respectively represent a scaling coefficient for the shape of the scanned object, θ represents a rotation angle for the shape of the scanned object, $t_x$ and $t_y$ respectively represent translation sizes of the control points for describing the shape of the scanned object in abscissa direction and ordinate direction.

5. The medical scanning method for determining scanning parameters according to claim 1, wherein the average shape is described based on the following equation:

$$\bar{s} = \frac{1}{N}\sum_{i=1}^{N} s_i$$

where, N represents a number of samples of scout images, s, is used for describing the shape of the scanned object in an $i^{th}$ sample of the initial scout image, 1≤i≤N.

6. The medical scanning method for determining scanning parameter according to claim 1, further comprising determining the desired shape with the maximum cost function value based on an optimization algorithm.

7. The medical scanning method for determining scanning parameters according to claim 1, wherein a desired shape acquisition module includes:
imparting a first plurality of weight parameters within a first varying range of numerical values to the principal component to acquire a plurality of first new shapes, and determine a better shape with a second maximum cost function value;
imparting a second plurality of weight parameters within a second varying range of numerical values that is less than the first varying range of numerical values to the principal component to acquire a plurality of second new shapes, wherein the second plurality of weight parameters is centered on a weight parameter of the better shape and determines the desired shape with the maximum cost function value.

8. A medical scanning method for determining scanning parameters, comprising:
arranging a plurality of control points for describing a shape of a scanned object on an initial scout image;
aligning the shape of the scanned object with a previously stored average shape by linearly transforming the plurality of control points for describing the shape of the scanned object;
extracting a principal component of the aligned shape of the scanned object based on a principal component analysis algorithm;
acquiring a plurality of new shapes by imparting a plurality of weight parameters to the principal component based on the following equation:

$$s' = \bar{s} + P_s b_{new}$$

where, s' is used to describe a new shape, $\bar{s}$ is used to describe an average shape, $P_s$ represents the principal component, $b_{new}$ represents the weight parameter of the principal component;
determining a desired shape with a maximum cost function value based on the plurality of new shapes; and
setting up scanning parameters based on the desired shape.

9. The medical scanning method for determining scanning parameters according to claim 8, further comprising:
in the initial scout image, determining a region of interest as an image of interest based on a gray-scale projection method.

10. The medical scanning method for determining scanning parameters according to claim 8, further comprising:
setting a starting point and an end point in the initial scout image based on operation instructions of an operating device, and defining, in the initial scout image, a region as an image of interest based on the starting point and the end point.

11. The medical scanning method for determining scanning parameters according to claim 8, further comprising linearly transforming a control point for describing the shape of the scanned object based on the following equation:

$$\begin{pmatrix} x' \\ y' \end{pmatrix} = \begin{bmatrix} s_x & 0 \\ 0 & s_y \end{bmatrix} \begin{bmatrix} \cos\theta & -\sin\theta \\ \sin\theta & \cos\theta \end{bmatrix} \begin{pmatrix} x \\ y \end{pmatrix} + \begin{pmatrix} t_x \\ t_y \end{pmatrix}$$

where, x' and y' respectively represent abscissa values and ordinate values of the linearly transformed control point for describing the shape of the scanned object on the initial scout image, x and y respectively represent abscissa values and ordinate values of the control points for describing the shape of the scanned object, before being linearly transformed, on the initial scout image, $s_x$ and $s_y$ respectively represent a scaling coefficient for the shape of the scanned object, θ represents a rotation angle for the shape of the scanned object, $t_x$ and $t_y$ respectively represent translation sizes of the linearly transformed control points for describing the shape of the scanned object in abscissa direction and ordinate direction.

12. The medical scanning method for determining scanning parameters according to claim 8, wherein an average shape is described based on the following equation:

$$\bar{S} = \frac{1}{N}\sum_{i=1}^{N} s_i$$

where, N represents a number of samples of scout images, $s_i$ is used for describing the shape of the scanned object in an $i^{th}$ sample of the initial scout image, $1 \le i \le N$.

13. The medical scanning method for determining scanning parameter according to claim 8, further comprising determining a desired shape with a maximum cost function value based on an optimization algorithm.

14. The medical scanning method for determining scanning parameters according to claim 8, further comprising:
imparting a first plurality of weight parameters within a first varying range of numerical values to the principal component to acquire a first plurality of new shapes, and determining, from the acquired first plurality of new shapes, a better shape with a second maximum cost function value;
imparting a second plurality of weight parameters within a second varying range of numerical values that is less than the first varying range of numerical values to said principal component to acquire a second plurality of new shapes, wherein the second plurality of weight parameters is centered on the weight parameter of the better shape, and determining a desired shape with the second maximum cost function value.

* * * * *

UNITED STATES PATENT AND TRADEMARK OFFICE
CERTIFICATE OF CORRECTION

PATENT NO. : 10,026,168 B2
APPLICATION NO. : 15/124336
DATED : July 17, 2018
INVENTOR(S) : Ping Liu, Jiaqin Dong and Jie Wu Page 1 of 1

It is certified that error appears in the above-identified patent and that said Letters Patent is hereby corrected as shown below:

In Claim 5, Line 48, correct "s," to read "$s_i$".

Signed and Sealed this
Twenty-eighth Day of August, 2018

Andrei Iancu
*Director of the United States Patent and Trademark Office*